United States Patent [19]

Noveroske

[11] Patent Number: 5,236,887
[45] Date of Patent: Aug. 17, 1993

[54] HERBICIDAL HETEROCYCLIC SULFONYLUREA COMPOSITIONS SAFENED BY HERBICIDAL ACIDS SUCH AS 2,4-D BELOW A PH OF 5

[75] Inventor: Robert L. Noveroske, Midland, Mich.

[73] Assignee: DowElanco, Indianapolis, Ind.

[21] Appl. No.: 695,194

[22] Filed: May 3, 1991

[51] Int. Cl.$^5$ .................. A01N 25/32; A01N 47/36; A01N 43/40; A01N 37/10
[52] U.S. Cl. ................... 504/105; 504/110; 504/130; 504/135; 504/136; 504/139
[58] Field of Search .............. 71/92, 117, 90, 93, 71/94, 115, 116; 504/105, 110, 130, 135, 136, 139

[56] References Cited

U.S. PATENT DOCUMENTS

| | | | |
|---|---|---|---|
| 3,131,509 | 5/1964 | Hoffmann | 47/1 |
| 4,127,405 | 11/1978 | Levitt | 71/93 |
| 4,170,464 | 10/1979 | Feeny | 71/110 |
| 4,383,113 | 5/1983 | Levitt | 544/211 |
| 4,394,506 | 7/1983 | Levitt | 544/321 |
| 4,547,215 | 10/1985 | Wolf | 71/92 |
| 4,605,433 | 8/1986 | Pearson et al. | 71/93 |
| 4,731,466 | 3/1988 | Staiger et al. | 560/75 |
| 4,840,663 | 6/1989 | Quadranti et al. | 71/93 |
| 4,936,900 | 6/1990 | Hyson | 71/90 |
| 5,010,195 | 4/1991 | Van Heertum et al. | 544/263 |

FOREIGN PATENT DOCUMENTS 0142152  11/1984  European Pat. Off. .

Primary Examiner—Richard L. Raymond
Assistant Examiner—S. Mark Clardy
Attorney, Agent, or Firm—S. Preston Jones

[57] ABSTRACT

Disclosed are herbicidal concentrate formulation compositions having reduced grass crop plant phytotoxicity comprising certain sulfonamide or sulfonylurea herbicides in admixture with a herbicidal organic acid from the group consisting of clopyralid, 2,4-D, 2,4-DP, dicamba, dichlorprop-P, fluroxypyr MCPA, MCPP, mecoprop-P, picloram, triclopyr or mixtures of said acids; also disclosed is the preparation of said compositions and the pre- and post-emergent agricultural uses thereof in water diluted form.

150 Claims, No Drawings

HERBICIDAL HETEROCYCLIC SULFONYLUREA COMPOSITIONS SAFENED BY HERBICIDAL ACIDS SUCH AS 2,4-D BELOW A PH OF 5

FIELD OF THE INVENTION

The present invention is directed to herbicidal concentrate formulation compositions comprising certain sulfonamide or sulfonylurea herbicides in admixture with a herbicidal organic acid from the group consisting of clopyralid, 2,4-D, 2,4-DP (dichlorprop) and its optical isomer (dichlorprop-P), dicamba, fluroxypyr, 4-chloro-2-methylphenoxyacetic acid (MCPA), 2-(4-chloro-2-methylphenoxy)propionic acid (MCPP) and its optical isomer (mecoprop-P), picloram, and triclopyr or mixtures of said acids; in addition, the present invention also is directed to the preparation of said concentrates and the pre- and post-emergent agricultural uses of said concentrates in water diluted formulations which formulations have a pH of below 5.

BACKGROUND OF THE INVENTION

Various herbicides, such as, for example, those of the sulfonamide and sulfonylurea classes are known to be active as selective pre- and post-emergent weed control agents. Many times when certain of these compounds are employed at the dosage rates usually necessary for the control of many of the broadleaf and/or grassy weeds, serious loss of many grass crop plants occur.

One procedure to overcome the above indicated sensitivity responses of plants to the various herbicidal compounds involves varying the dosage rate. When a reduction in the dosage rate is used to avoid phytotoxicity to the crop plants, reduced weed control is often the result.

Another procedure involves changing the time of application or modifying the ingredients used in the formulations containing the active compound. Other known procedures include treatment of the seeds of the crop plants with an agent antagonistic to the herbicide prior to planting as described in U.S. Pat. No. 3,131,509.

It has now been found that the pre- and post-emergent phytotoxicity of certain sulfonamide and sulfonylurea herbicides towards grass crop plants is reduced by admixing said herbicides with a herbicidal organic acid in an amount sufficient to reduce the pH of the mixture to below 5. The herbicidal acids are from the group consisting of clopyralid, 2,4-D, 2,4-DP and its optical isomer dichlorprop-P, dicamba, fluroxypyr, MCPA, MCPP and its optical isomer mecoprop-P, picloram, and triclopyr or mixtures of said acids. It has further been discovered that the known salts and esters of these acids do not offer the same protection to the crop plants as afforded by the acid form of said compounds.

DESCRIPTION OF KNOWN PRIOR ART

U.S. Pat. No. 4,127,405 is directed to certain sulfonamides and their use as selective herbicides. It is further indicated that the claimed compounds can be used in combination with other herbicides and 2,4-D is listed. It is noted that no pH of the herbicide formulation is set forth.

U.S. Pat. No. 4,547,215 is directed to certain sulfonamides and their use as selective pre- or post-emergent herbicides. It is further indicated that the claimed compounds can be used in combination with other herbicides and list about 70 different herbicides including 2,4-D, dicamba, MCPA and MCPP. It is noted that no pH of the herbicide formulation is set forth.

U.S. Pat. No. 4,840,663 teaches the control of weeds in rice by the use of a synergistic mixture of N-(2-(2-methoxyethoxy)phenylsulfonyl)-N'-(4,6-dimethoxy-1,3,5-triazin-2-yl)urea and a herbicidal compound selected from a large grouping of different types of herbicides. One of the grouping includes 2,4-D acid and MCPA. It is noted that no pH of the herbicide formulation is set forth.

U.S. Pat. No. 4,936,900 is directed to stabilized compositions having a pH of 6-10 and containing a mixture of a sulfonylurea or one of its agriculturally suitable salts with a salt or mixture of salts of a carboxylic or inorganic acid. It is further indicated that other herbicides may be added to the mixture and a very large list of other herbicides which may be added is set forth which includes, for example, 2,4-D and its agriculturally suitable salts and esters, dicamba, MCPA and MCPP.

SUMMARY OF THE INVENTION

The present invention is directed to herbicidal concentrate compositions containing certain sulfonamide or sulfonylurea herbicides in admixture with a herbicidal organic acid from the group consisting of 2,4-D, 2,4-DP (dichlorprop) and its optical isomer (dichlorprop-P), MCPA, MCPP and its optical isomer (mecoprop-P), dicamba, picloram, clopyralid, fluroxypyr and triclopyr or mixtures of said acids. The invention is also directed to the preparation of said concentrates, aqueous formulations having a pH of below 5 prepared from said concentrates and the agricultural uses of the thus prepared formulations by applying herbicidally effective amounts of said formulations to plants or their habitat in the pre- and post-emergent kill and control of the weeds present in many grass crops.

DESCRIPTION OF SOME PREFERRED EMBODIMENTS

The compositions of the present invention have been found to possess desirable herbicidal activity for use in the pre- and post-emergent control of many broadleaf weeds such as velvetleaf, lambsquarter, kochia, pigweed, cocklebur, and buckwheat while showing high selectivity to important grass crops such as wheat, barley, sorghum, rice and corn.

The sulfonamide and sulfonylurea herbicides useful in the practice of the present invention are known. Many are articles of commerce and others are taught in patents, such as for example, U.S. Pat. Nos. 4,127,405; 4,383,113; 4,394,506; 4,605,433; 4,731,466 and 5,010,195 and European Application 0142152, published May 22, 1985. The specific sulfonamide and sulfonylurea herbicides used herein are selected from the group consisting of the compounds:

Ally (Metsulfuron-methyl):
    methyl 2-((4-methoxy-6-methyl-1,3,5-triazin-2-yl)ureidosulfonyl)benzoate;
Classic: (Chlorimuron-ethyl):
    ethyl 2-(((((4-chloro-6-methoxypyrimidin-2-yl)amino)carbonyl)amino)sulfonyl) benzoate;
Express/Granstar (Tribenuron-methyl):
    methyl 2-(((((4-methoxy-6-methyl-1,3,5-triazin-2-yl)methylamino)-carbonyl)amino)sulfonyl)benzoate;
Glean (Chlorsulfuron);

1-(2-chlorophenylsulfonyl)-3-(4-methoxy-6-methyl-1,3,5-triazin-2-yl)urea;

Harmony (Thifensulfuron):
3-((((N-(4-methoxy-6-methyl-1,3,5-triazin-2-yl)amino)carbonyl)amino)sulfonyl)-2-thiophenecarboxylic acid;

N-(2,6-dichloro-3-methylphenyl)-5,7-dimethoxy-1,2,4-triazolo-(1,5-a)pyrimidine-2-sulfonamide;

N-(2,6-difluorophenyl)-5-methyl-1,2,4-triazolo-(1,5-a)pyrimidine-2-sulfonamide;

N-(2,6-dichlorophenyl)-5-ethoxy-7-fluoro-1,2,4-triazolo-(1,5-c)-pyrimidine-2-sulfonamide;

2-(((7-fluoro-5-ethoxy-1,2,4-triazolo(1,5-c)pyrimidin-2-yl)sulfonyl)amino)-3-fluorobenzoic acid, methyl ester;

N-(2,6-difluorophenyl)-8-chloro-5-methoxy-1,2,4-triazolo-(1,5-c)pyrimidine-2-sulfonamide;

N-(2,6-difluorophenyl)-5-methoxy-8-fluoro-1,2,4-triazolo-(1,5-c)pyrimidine-2-sulfonamide, and N-(2-chloro-6-fluorophenyl)-5-ethoxy-7-fluoro-1,2,4-triazolo-(1,5-c)pyrimidine-2-sulfonamide;

The herbicidal acids which are usable in the practice of the present invention are selected from the group consisting of:

Clopyralid: 3,6-dichloro-2-pyridinecarboxylic acid, a well known herbicide in general commerce;

2,4-D: 2,4-dichlorophenoxyacetic acid, a well known herbicide in general commerce;

2,4-DP: 2-(2,4-dichlorophenoxy)propionic acid (dichlorprop) and its optical isomer (R)2-(2,4-dichlorophenoxy)propionic acid (dichlorprop-P); are well known herbicides in general commerce;

Dicamba: 3,6-dichloro-2-methoxybenzoic acid, a well known herbicide in general commerce;

Fluroxypyr: 4-amino-3,5-dichloro-6-fluoro-2-pyridinyloxyacetic acid, taught in U.S. Pat. No. 3,761,486;

MCPA: 4-chloro-2-methylphenoxyacetic acid, a well known herbicide in general commerce;

MCPP: 2-(4-chloro-2-methylphenoxy)propionic acid (mecoprop) and its optical isomer (mecoprop-P), a well known herbicide in general commerce;

Picloram: 4-amino-3,5,6-trichloropicolinic acid; and

Triclopyr: 3,5,6-trichloro-2-pyridinyloxyacetic acid, a well known herbicide in general commerce;

or mixtures of said acids.

The herbicidally effective amount of the active sulfonamide or sulfonylurea herbicide in the concentrate composition generally is from about 0.5 to about 90 percent by weight or more. Concentrations from about 2 to about 50 percent by weight are often preferred. The amount of said herbicide present in the final treating composition (mixture) is usually sufficient to provide during post-emergent control of broadleafed weeds from about 1.0 to about 70.0 grams of the said active material per hectare, preferably from about 2.0 to about grams of the said active material per hectare; for pre-emergent control of broadleafed weeds, the active herbicide is provided in an amount of about 10 to about 200 g ai/hectare.

The amount of acid present in the concentrate composition is generally from about 0.5 to about 80 percent by weight or more. The amount of acid present in the final treating composition (mixture) is sufficient to maintain the pH of the mixture below about 5.0 and usually from about pH 4.0 to about 2.5 acid and is usually present in an amount sufficient to provide during application, from about 15 to about 1200 grams of acid equivalent per hectare.

It is frequently desirable to incorporate a surface active agent in the composition of the present invention. Such surface active or wetting agents can be any of the anionic, cationic or nonionic normally employed in herbicidal formulations. A suitable list for reference may be found in "McCutcheon's Emulsifiers and Detergents" (1981 Edition).

Examples of anionic surfactants are the calcium and amine salts of dodecylbenzene sulfonic acid and sodium diisooctylsulfosuccinate.

Examples of nonionic surfactants are the condensation products of fatty acid esters, fatty alcohols, fatty acid amides or fatty amines with ethylene and/or propylene oxide, alkyl, alkenyl, or polyaryl-substituted phenols with ethylene and/or propylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, ethoxylated lanolin alcohols or ethoxylated lanolin acids.

Representative of the above surface active or wetting agents useful in the practice of the present invention include products such as, for example:

PG 26-2: a secondary butyl(((phenoxy(polypropylene)oxy)polyethylene)oxy) ethanol(5 moles E0,4 moles PO) a product of The Dow Chemical Co.

Triton (Ortho) X-77 alkylarylpolyoxyethylene glycol, a product of Chevron Chemical Co.

Silwet L-77: nonionic silicone glycol copolymer; a product of Union Carbide Corp.

Examples of a cationic agent include, for instance, an aliphatic mono-, di- or polyamine as an acetate or oleate.

Anionic/nonionic blends are preferred and are often advantageously chosen as pre-blended systems for ease of handling, reproducibility and cost effectiveness.

The choice of suitable surfactants are well within the capabilities of one skilled in the art.

The amount of surfactant present in the concentrate composition will generally be in the range of from about 0.0 percent to about 10 percent, preferably from 1.0 percent to 5.0 percent by weight. The amount of surfactant present in the final treating composition (mixture) is usually from about 0.0 to about 5.0 percent by weight, preferably from 0.0 percent to 0.5 percent by weight.

In the agricultural uses set forth hereinabove, the present invention also embraces the employment of the present herbicides in combination with one or more additional pesticidal compounds. Such additional pesticidal compounds may be other types of herbicides, insecticides, nematocides, miticides, arthropodicides, fungicides or bactericides that are compatible with the compounds of the present invention in the aqueous medium used for application and which are not antagonistic to the activity of the compounds employed in the present concentrate. Accordingly, in such embodiments, the additional pesticidal compound(s) is employed as a supplemental toxicant or as an additament. The added compounds in combination with the compounds of the concentrate can generally be present in a ratio of from 1 to 100 parts of the compounds of concentrate of the present invention with from 100 to 1 part of the additional compound.

The exact herbicidally effective amount of the composition to be applied is also dependent not only on the specific active ingredient contained therein, but also on the particular action desired, the plant species to be controlled, the stage of growth thereof as well as the specific part of the plant to be contacted or type of growth medium in which the seeds are planted.

The following examples illustrate the present invention and the manner by which it can be practiced but, as such, should not be construed as limitations upon the overall scope of the same. In all tests, the herbicidal acid employed is always in its acid form. In addition, the pH value given is taken from the run with the highest acid concentration and the pH of all runs is less than 5.0.

EXAMPLE I

Representative compositions of the present invention were evaluated to determine their phytotoxicity effect in post-emergent operations on corn plants.

Aqueous dispersions were prepared by admixing a predetermined amount of one of the hereinafter set forth compounds with a predetermined quantity of water, a predetermined amount of 2,4-D and a predetermined amount of the surfactant X-77 to give aqueous dispersions containing varying amounts of one of the compounds, as the sole toxicant.

Corn seeds were planted in beds of good agricultural peat based growth medium and grown in a greenhouse. After the plants had emerged and had grown to a height of about 4 inches, separate beds of the plants were sprayed with one of the above-prepared compositions at predetermined treating rates in grams of the active ingredient per hectare (g ai/ha). Other beds were treated only with a water-surfactant mixture (control), containing no active compound, and others containing the active compound and surfactant, but no acid, to serve as controls. After treatment, the beds were maintained for about one week under greenhouse conditions conducive for good plant growth. At the end of this period after treatment, the beds were examined to determine the percentage of phytotoxicity to the corn plants. The results of these examinations are set forth below in Table I.

EXAMPLE II

Representative compositions of the present invention were evaluated to determine their phytotoxicity effect in post-emergent operations on corn plants.

Aqueous dispersions containing hifensulfuron, as the active ingredient, were prepared by admixing a predetermined amount of the compound with a predetermined quantity of water, a predetermined amount of one of 2,4-D, MCPA or MCPP and a predetermined amount of the surfactant X-77 to give aqueous dispersions containing varying amounts of the compound, as the sole toxicant.

Corn seeds were planted in beds of good agricultural peat based growth medium and grown in a greenhouse. After the plants had emerged and had grown to a height of about 4 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for five days under greenhouse conditions conducive for good plant growth. At the end of this period, the beds were examined to determine the percentage of phytotoxicity to the corn plants. The results of these examinations are set forth below in Table II.

TABLE II

| Test mixture | Treating Rate in g ae/ha* | pH | % Growth reduction as a % of control at indicated g ai/ha** | | |
|---|---|---|---|---|---|
| | | | 17.5 | 8.8 | 4.4 |
| Compound/NA | 0.0 | 7.21 | 45,0 | 35.0 | 20.0 |
| Compound + 2,4-D | 140.00 | 3.24 | 7.5 | 2.5 | 0.0 |
| | 70.00 | 3.65 | 7.5 | 5.0 | 5.0 |
| Compound + MCPA | 140.00 | 3.30 | 25.0 | 20.0 | 10.0 |
| | 70.00 | 3.68 | 25.0 | 20.0 | 10.0 |
| Compound + MCPP | 140.00 | 3.39 | 25.0 | 20.0 | 10.0 |
| | 70.00 | 3.91 | 25.0 | 20.0 | 15.0 |

TABLE I

| Test mixture | Treating Rate in g ae/ha* | pH | % growth reduction as a % of control at indicated g ai/ha** | | | | |
|---|---|---|---|---|---|---|---|
| | | | 17.5 | 8.8 | 4.4 | 2.2 | 1.1 |
| Metsulfuron-methyl/NA | 0.0 | 7.43 | — | — | 65.0 | 60.0 | 30.0 |
| Metsulfuron-methyl + 2,4-D | 280.0 | 2.97 | — | — | 50.0 | 15.0 | 5.0 |
| Chlorsulfuron/NA | 0.0 | 6.84 | — | — | 50.0 | 50.0 | 50.0 |
| Chlorsulfuron + 2,4-D | 280.0 | 2.98 | — | — | 45.0 | 30.0 | 20.0 |
| Chlorimuron-ethyl/NA | 0.0 | 7.24 | — | 40.0 | 40.0 | 30.0 | — |
| Chlorimuron-ethyl + 2,4-D | 280.00 | 2.94 | — | 20.0 | 10.0 | 5.0 | — |
| Thifensulfuron/NA | 0.0 | 7.49 | 65.0 | 35.0 | 35.0 | — | — |
| Thifensulfuron + 2,4-D | 280.00 | 2.93 | 10.0 | 5.0 | 5.0 | — | — |
| Tribenuron-methyl/NA | 0.0 | 7.44 | 50.0 | 50.0 | 45.0 | — | — |
| Tribenuron-methyl + 2,4-D | 280.00 | 2.97 | 10.0 | 5.0 | 5.0 | — | — |
| control | — | 6.85 | 0.0 | 0.0 | 0.0 | 0.0 | 0.0 |

NA = no acid control
*grams of acid equivalent per hectare.
**grams of active ingredient per hectare.

TABLE II-continued

| Test mixture | Treating Rate in g ae/ha* | pH | % Growth reduction as a % of control at indicated g ai/ha** | | |
|---|---|---|---|---|---|
| | | | 17.5 | 8.8 | 4.4 |
| control | — | 7.34 | 0.0 | 0.0 | 0.0 |

NA = no acid control
*grams of acid equivalent per hectare.
**grams of active ingredient per hectare.

EXAMPLE III

Representative compositions of the present invention were evaluated to determine their phytotoxicity effect in post-emergent operations on wheat plants.

Aqueous dispersions containing N-(2,6-dichloro-3-methylphenyl)-5,7-dimethoxy-1,2,4-triazolo-(1,5-a)pyrimidine-2-sulfonamide, as the active ingredient, were prepared by admixing a predetermined amount of the compound with a predetermined quantity of water, a predetermined amount of one of 2,4-D, MCPA or MCPP and a predetermined amount of the surfactant X-77 to give aqueous dispersions having an acid equivalent of 280 g ae/ha and containing varying amounts of the compound, as the sole toxicant.

Wheat seeds were planted in beds of good agricultural peat based growth medium and grown in a greenhouse. After the plants had emerged and had grown to a height of about 4–5 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for five days under greenhouse conditions conducive for good plant growth. At the end of this period, the beds were examined to determine the percentage of phytotoxicity to the wheat plants. The results of these examinations are set forth below in Table III.

TABLE III

| Test mixture | Treating Rate in g ae/ha* | pH | % leaf shedding as a % of control at indicated g ai/ha** | | |
|---|---|---|---|---|---|
| | | | 35.0 | 17.5 | 8.8 |
| Compound/NA | 0.0 | 7.44 | 10.3 | 11.8 | 14.7 |
| Compound + 2,4-D | 140.00 | 3.43 | 0.0 | 1.5 | 0.0 |
| | 70.00 | 3.65 | 2.9 | 2.9 | 0.0 |
| Compound + MCPA | 140.00 | 3.07 | 0.0 | 1.5 | 7.4 |
| | 70.00 | 3.32 | 0.0 | 2.9 | 1.5 |
| Compound + MCPP | 140.00 | 3.24 | 1.5 | 1.5 | 2.9 |
| | 70.00 | 3.53 | 2.9 | 1.5 | 0.0 |
| control | — | 7.78 | 0.0 | 0.0 | 0.0 |

NA = no acid control
*grams of acid equivalent per hectare.
**grams of active ingredient per hectare.

EXAMPLE IV

Representative compositions of the present invention were evaluated to determine their phytotoxicity effect in post-emergent operations on corn plants.

Aqueous dispersions containing one of N-(2,6-dichlorophenyl)-5-ethoxy-7-fluoro-1,2,4-triazolo(1,5-c)-pyrimidine-2-sulfonamide (Compound A); 2-(((7-fluoro-5-ethoxy-1,2,4-triazolo-(1,5-c)-pyrimidin-2-yl)sulfonyl)amino)-3-fluorobenzoic acid; methyl ester (Compound B); N-(2-chloro-6-fluorophenyl)-5-ethoxy-7-fluoro-1,2,4-triazolo-(1,5-c)pyrimidine-2-sulfonamide (Compound C) or Thifensulfuron (Compound D), as the active ingredient, were prepared by admixing a predetermined amount of the compound with a predetermined quantity of water, a predetermined amount of 2,4-D and a predetermined amount of the surfactant X-77 to give aqueous dispersions containing varying amounts of one of the compounds, as the sole toxicant.

Corn seeds were planted in beds of good agricultural peat based growth medium and grown in a greenhouse. After the plants had emerged and had grown to a height of about 4 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for seven days under greenhouse conditions conducive for good plant growth. At the end of this period, the beds were examined to determine the percentage of phytotoxicity to the corn plants. The results of these examinations are set forth below in Table IV.

TABLE IV

| Test mixture | Treating Rate in g ae/ha* | pH | % growth reduction as a % of control at indicated g ai/ha** | | |
|---|---|---|---|---|---|
| | | | 17.5 | 8.8 | 4.4 |
| Compound/NA | 0.0 | 6.62 | 50.0 | 50.0 | 45.0 |
| Compound A + 2,4-D | 280.0 | 3.00 | 25.0 | 20.0 | 10.0 |
| Compound B/NA | 0.0 | 6.63 | 30.0 | 30.0 | 25.0 |
| Compound B + 2,4-D | 280.0 | 3.01 | 20.0 | 10.0 | 10.0 |
| Compound C/NA | 0.0 | 6.60 | 30.0 | 30.0 | 25.0 |
| Compound C + 2,4-D | 280.00 | 3.02 | 5.0 | 5.0 | 5.0 |
| Compound D/NA | 0.0 | 7.39 | 40.0 | 35.0 | 20.0 |
| Compound D + 2,4-D | 280.00 | 2.99 | 10.0 | 5.0 | 0.0 |
| control | — | 7.51 | 0.0 | 0.0 | 0.0 |

NA = no acid control
*grams of acid equivalent per hectare.
**grams of active ingredient per hectare.

EXAMPLE V

Representative compositions of the present invention were evaluated to determine their phytotoxicity effect in post-emergent operations on corn plants.

Aqueous dispersions containing one of N-(2,6-difluorophenyl)-5-methyl-1,2,4-triazolo-(1,5-a)pyrimidine-2-sulfonamide or Thifensulfuron, as the active ingredient, were prepared by admixing a predetermined amount of the compound with a predetermined quantity of water, a predetermined amount of 2,4-D and a predetermined amount of the surfactant X-77 to give aqueous dispersions containing varying amounts of one of the compounds, as the sole toxicant.

Corn seeds were planted in beds of good agricultural peat based growth medium and grown in a greenhouse. After the plants had emerged and had grown to a height of about 4 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for seven days under greenhouse conditions conducive for good plant growth. At the end of this period, the beds were examined to determine the percentage of phytotoxicity to the corn plants. The results of these examinations are set forth below in Table V.

TABLE V

| Test mixture | Treating Rate in g ae/ha* | pH | % growth reduction as a % of control at indicated g ai/ha** | | | |
|---|---|---|---|---|---|---|
| | | | 35.0 | 17.5 | 8.8 | 4.4 |
| N-(2,6-difluoro-phenyl)-5-methyl-1,2,4-triazolo-(1,5-a)-pyrimidine-2-sulfonamide/NA | 0.0 | 7.48 | 10.0 | 10.0 | 10.0 | — |
| N-(2,6-difluorophenyl)-5-methyl-1,2,4-triazolo-(1,5-a)-pyrimidine-2-sulfonamide + 2,4-D | 280.00 | 3.08 | 0.0 | 0.0 | 0.0 | — |
| N-(2,6-difluorophenyl)-5-methyl-1,2,4-triazolo-(1,5-a)-pyrimidine-2-sulfonamide + 2,4-D | 70.00 | 3.62 | 5.0 | 5.0 | 5.0 | — |
| Thifensulfuron/NA | 0.0 | 7.84 | — | 60.0 | 40.0 | 30.0 |
| Thifensulfuron + 2,4-D | 280.00 | 3.09 | — | 10.0 | 10.0 | 5.0 |
| Thifensulfuron + 2,4-D | 140.00 | 3.24 | — | 5.0 | 5.0 | 5.0 |
| Thifensulfuron + 2,4-D | 70.00 | 3.65 | — | 0.0 | 0.0 | 0.0 |
| control | — | 7.83 | 0.0 | 0.0 | 0.0 | 0.0 |

NA = no acid control
*grams of acid equivalent per hectare.
**grams of active ingredient per hectare.

EXAMPLE VI

Representative compositions of the present invention were evaluated to determine their phytotoxicity effect in post-emergent operations on both corn and wheat plants.

Aqueous dispersions containing one of N-(2,6-difluorophenyl)-5-methyl-1,2,4-triazolo-(1,5-a)pyrimidine-2-sulfonamide or N-(2,6-dichloro-3-methylphenyl)-5,7-dimethoxy-1,2,4-triazolo-(1,5-a)pyrimidine-2-sulfonamide, as the active ingredient, were prepared by admixing a predetermined amount of the compound with a predetermined quantity of water, a predetermined amount of each of 2,4-D and fluroxypyr and a predetermined amount of the surfactant X-77 to give aqueous dispersions containing one of the compounds, as the sole toxicant.

Corn and wheat seeds were planted in beds of good agricultural peat based growth medium and grown in a greenhouse. After the plants had emerged and had 1 grown to a height of about 4–5 inches, separate beds of the plants were sprayed with one of the above-prepared compositions at treating rates of 17.5 g ai/ha. Other beds were treated only with a water-surfactant mixture, containing no active compound, and others containing the active compound and surfactant, but no acid, to serve as controls. After treatment, the beds were maintained for seven days under greenhouse conditions conducive for good plant growth. At the end of this period, the beds were examined to determine the percentage of phytotoxicity to the corn and wheat plants. The results of these examinations are set forth below in Table VI.

TABLE VI

| Test mixture | Treating Rate in g ae/ha* | pH | % growth reduction as a % of control | |
|---|---|---|---|---|
| | | | Corn | Wheat |
| N-(2,6-difluorophenyl)-5-methyl-1,2,4-triazolo-(1,5-a)-pyrimidine-2-sulfonamide/NA | 0.0 | 7.44 | 5.0 | 5.0 |
| N-(2,6-difluorophenyl)-5-methyl-1,2,4-triazolo-(1,5-a)-pyrimidine-2-sulfonamide + 2,4-D/fluroxypyr | 140.0/70.0 | 3.21 | 0.0 | 0.0 |
| N-(2,6-dichloro-3-methylphenyl)-5,7-dimethoxy-1,2,4-triazolo-(1,5-a)pyrimidine-2-sulfonamide/NA | 0.0 | 7.34 | 10.0 | 20.0 |
| N-(2,6-dichloro-3-methylphenyl)-5,7-dimethoxy-1,2,4-triazolo-(1,5-a)pyrimidine-2-sulfonamide +2,4-D/fluroxypyr | 140.0/70.0 | 3.42 | 5.0 | 0.0 |
| control | 0.0 | 7.92 | 0.0 | 0.0 |

NA = no acid control
*grams of acid equivalent per hectare.

EXAMPLE VII

Representative compositions of the present invention were evaluated to determine their phytotoxicity effect in post-emergent operations on wheat plants.

Aqueous dispersions containing N-(2,6-dichloro-3-methylphenyl)-5,7-dimethoxy-1,2,4-triazolo-(1,5-a)pyrimidine-2-sulfonamide, as the active ingredient, were prepared by admixing a predetermined amount of the compound with a predetermined quantity of water, a predetermined amount of one of 2,4-D or fluroxypyr and a predetermined amount of the surfactant X-77 to give aqueous dispersions containing the compound, as the sole toxicant.

Wheat seeds were planted in beds of good agricultural peat based growth medium and grown in a greenhouse. After the plants had emerged and had grown to a height of about 4–5 inches, separate beds of the plants were sprayed with one of the above-prepared compositions at treating rates of 17.5 g ai/ha. Other beds were treated only with a water-surfactant mixture, containing no active compound, and others containing the active compound and surfactant, but no acid, to serve as controls. After treatment, the beds were maintained for seven days under greenhouse conditions conducive for good plant growth. At the end of this period, the beds were examined to determine the percentage of phytotoxicity to the wheat plants as evidenced by leaf shedding. The results of these examinations are set forth below in Table VII.

TABLE VII

| Test mixture | Treating Rate in g ae/ha* | pH | % leaf shedding of wheat plants Wheat |
|---|---|---|---|
| N-(2,6-dichloro-3-methylphenyl)-5,7-dimethoxy-1,2,4-triazolo-(1,5-a)pyrimidine-2-sulfonamide/NA | 0.0 | 7.28 | 9.1 |
| N-(2,6-dichloro-3-methylphenyl)-5,7-dimethoxy-1,2,4-triazolo-(1,5-a)pyrimidine-2-sulfonamide + 2,4-D | 140.0 | 3.35 | 0.0 |
| N-(2,6-dichloro-3-methylphenyl)-5,7-dimethoxy-1,2,4- | 70.0 | 4.19 | 5.9 |

TABLE VII-continued

| Test mixture | Treating Rate in g ae/ha* | pH | % leaf shedding of wheat plants Wheat |
| --- | --- | --- | --- |
| triazolo-(1,5-a)pyrimidine-2-sulfonamide + fluroxypyr | | | |
| N-(2,6-dichloro-3-methylphenyl)-5,7-dimethoxy-1,2,4-triazolo-(1,5-a)pyrimidine-2-sulfonamide + 2,4-D + fluroxypyr | 140/70.0 | 3.30 | 0.0 |
| control | 0.0 | 7.92 | 0.0 |

NA = no acid control
*grams of acid equivalent per hectare.

EXAMPLE VIII

Representative compositions of the present invention were evaluated to determine their effectiveness in post-emergent operations.

Aqueous dispersions were prepared by admixing a predetermined amount of N-(2,6-dichloro-3-methylphenyl)-5,7-dimethoxy-1,2,4-triazolo-(1,5-a)pyrimidine-2-sulfonamide with a predetermined amount of 2,4-D and a predetermined amount of the surfactant X-77 to give aqueous dispersions containing varying amounts of the compound.

Seeds of the weed species lambsquarter, buckwheat and velvetleaf were planted in beds of good agricultural growth medium and grown in a greenhouse. After the plants had emerged and had grown to a height of from 0.5-3 inches (depending on the plant species), separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for eighteen days under greenhouse conditions conducive for good plant growth. At the end of this period, the beds were examined to determine the percentage of kill and control of the above listed weeds. The results of these examinations are set forth below in Table VIII.

TABLE VIII

| Test mixture | Treating Rate in g ae/ha | Treating Rate in g ai/ha | pH | % kill and control of the plants | | |
| --- | --- | --- | --- | --- | --- | --- |
| | | | | lambsquarter | buckwheat | velvetleaf |
| N-(2,6-dichloro-3-methylphenyl)-5,7-dimethoxy-1,2,4-triazolo-(1,5-a)pyrimidine-2-sulfonamide/NA | — | 17.5 | 7.12 | 70.0 | 85.0 | 75.0 |
| N-(2,6-dichloro-3-methylphenyl)-5,7-dimethoxy-1,2,4-triazolo-(1,5-a)pyrimidine-2-sulfonamide/NA | — | 5.8 | 7.45 | 60.0 | 82.5 | 60.0 |
| N-(2,6-dichloro-3-methylphenyl)-5,7-dimethoxy-1,2,4-triazolo-(1,5-a)pyrimidine-2-sulfonamide + 2,4-D | 140.0 | 17.5 | 3.31 | 98.0 | 100.0 | 99.2 |
| N-(2,6-dichloro-3-methylphenyl)-5,7-dimethoxy-1,2,4-triazolo-(1,5-a)pyrimidine-2-sulfonamide + 2,4-D | 46.7 | 5.8 | 4.07 | 95.0 | 85.0 | 83.5 |
| control | 0.0 | 0.0 | 7.92 | 0.0 | 0.0 | 0.0 |

NA = no acid control

EXAMPLE IX

Representative compositions of the present invention were evaluated to determine their phytotoxicity effect in post-emergent operations on wheat plants.

Aqueous dispersions containing N-(2,6-dichloro-3-methylphenyl)-5,7-dimethoxy-1,2,4-triazolo-(1,5-a)pyrimidine-2-sulfonamide, as the active ingredient, were prepared by admixing a predetermined amount of the compound with a predetermined quantity of water, a predetermined amount of one of 2,4-D or triclopyr and a predetermined amount of the surfactant X-77 to give aqueous dispersions containing the compound, as the sole toxicant.

Wheat seeds were planted in beds of good agricultural peat based growth medium and grown in a greenhouse. After the plants had emerged and had grown to a height of about 5 inches, separate beds of the plants were sprayed with one of the above-prepared compositions at treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for seven days under greenhouse conditions conducive for good plant growth. At the end of this period, the beds were examined to determine the percentage of phytotoxicity to the wheat plants as evidenced by leaf shedding. The results of these examinations are set forth below in Table IX.

TABLE IX

| Test mixture | Treating Rate in g ae/ha* | pH | % leaf shedding of wheat plants at indicated treating rates in ai/ha | |
| --- | --- | --- | --- | --- |
| | | | 17.5 | 5.8 |
| N-(2,6-dichloro-3-methylphenyl)-5,7-dimethoxy-1,2,4-triazolo-(1,5-a)pyrimidine-2-sulfonamide/NA | 0.0 | 7.4 | 19.4 | 17.9 |
| N-(2,6-dichloro-3-methylphenyl)-5,7-dimethoxy-1,2,4-triazolo- | 140.0 | 3.2 | 10.5 | — |

TABLE IX-continued

| Test mixture | Treating Rate in g ae/ha* | pH | % leaf shedding of wheat plants at indicated treating rates in ai/ha | |
| --- | --- | --- | --- | --- |
| | | | 17.5 | 5.8 |
| (1,5-a)pyrimidine-2-sulfonamide + 2,4-D | | | | |
| N-(2,6-dichloro-3-methylphenyl)-5,7-dimethoxy-1,2,4-triazolo-(1,5-a)pyrimidine-2-sulfonamide + 2,4-D | 46.6 | 4.1 | — | 13.0 |
| N-(2,6-dichloro-3-methylphenyl)-5,7-dimethoxy-1,2,4-triazolo-(1,5-a)pyrimidine-2-sulfonamide + triclopyr | 140.0 | 3.6 | 9.8 | — |
| N-(2,6-dichloro-3-methylphenyl)-5,7-dimethoxy-1,2,4-triazolo-(1,5-a)pyrimidine-2-sulfonamide + triclopyr | 46.6 | 5.5 | — | 5.7 |
| control | 0.0 | 7.5 | 0.0 | 0.0 |

NA = no acid control
*grams of acid equivalent per hectare.

EXAMPLE X

Representative compositions of the present invention were evaluated to determine their phytotoxicity effect in post-emergent operations on wheat plants.

Aqueous dispersions containing N-(2,6-dichloro-3-methylphenyl)-5,7-dimethoxy-1,2,4-triazolo-(1,5-a)-pyrimidine-2-sulfonamide, as the active ingredient, were prepared by admixing a predetermined amount of the compound with a predetermined quantity of water, a predetermined amount of one of 2,4-D, clopyralid or picloram and a predetermined amount of the surfactant X-77 to give aqueous dispersions containing varying amounts of the compound, as the sole toxicant.

Wheat seeds were planted in beds of good agricultural peat based growth medium and grown in a greenhouse. After the plants had emerged and had grown to a height of about 5 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for eight days under greenhouse conditions conducive for good plant growth. At the end of this period, the beds were examined to determine the percentage of phytotoxicity to the wheat plants. The results of these examinations are set forth below in Table X.

TABLE X

| Test mixture | Treating Rate in g ae/ha* | pH | % Growth reduction as a % of control at indicated g ai/ha** | |
| --- | --- | --- | --- | --- |
| | | | 35.0 | 8.8 |
| Compound/NA | 0.0 | 7.34 | 25.0 | 20.0 |
| Compound + 2,4-D | 140.00 | 3.20 | 5.0 | 0.0 |
| | 70.00 | 3.30 | 15.0 | 0.0 |
| Compound + clopyralid | 140.00 | 2.73 | 5.0 | 0.0 |
| | 70.00 | 3.08 | 5.0 | 0.0 |
| Compound + picloram | 140.00 | 2.87 | 15.0 | 5.0 |
| | 70.00 | 3.35 | 20.0 | 15.0 |
| control | — | 7.34 | 0.0 | 0.0 |

NA = no acid control
*grams of acid equivalent per hectare.
**grams of active ingredient per hectare.

EXAMPLE XI

Representative compositions of the present invention were evaluated to determine their phytotoxicity effect in post-emergent operations on corn plants.

Aqueous dispersions containing N-(2,6-dichloro-3-methylphenyl)-5-ethoxy-7-fluoro-1,2,4-triazolo-1,5-c)-pyrimidine-2-sulfonamide, as the active ingredient, were prepared by admixing a predetermined amount of the compound with a predetermined quantity of water, a predetermined amount of one of 2,4-D, clopyralid, triclopyr or picloram and a predetermined amount of the surfactant X-77 to give aqueous dispersions containing 15 varying amounts of the compound, as the sole toxicant.

Corn seeds were planted in beds of good agricultural peat based growth medium and grown in a greenhouse. After the plants had emerged and had grown to a height of about 4 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for twelve days under greenhouse conditions conducive for good plant growth. At the end of this period, the beds were examined to determine the percentage of phytotoxicity to the corn plants. The results of these examinations are set forth below in Table XI.

TABLE XI

| Test mixture | Treating Rate in g ae/ha* | pH | % Growth reduction as a % of control at indicated g ai/ha** | |
| --- | --- | --- | --- | --- |
| | | | 8.8 | 2.2 |
| Compound/NA | 0.0 | 7.43 | 70.0 | 30.0 |
| Compound + 2,4-D | 140.00 | 3.37 | 30.0 | 0.0 |
| Compound + clopyralid | 140.00 | 2.74 | 35.0 | 10.0 |
| Compound + triclopyr | 140.00 | 3.50 | 45.0 | 20.0 |
| Compound + picloram | 140.00 | 3.12 | 45.0 | 15.0 |
| control | — | 7.43 | 0.0 | 0.0 |

NA = no acid control
*grams of acid equivalent per hectare.
**grams of active ingredient per hectare.

EXAMPLE XII

Representative compositions of the present invention were evaluated to determine their phytotoxicity effect in post-emergent operations on corn, sorghum and wheat plants.

Aqueous dispersions containing one of N-(2,6-difluorophenyl-5-methyl-1,2,4-triazolo-(1,5-a)-pyrimidine-2-sulfonamide (Compound 1), N-(2,6-difluorophenyl)-5-methoxy-8-fluoro-1,2,4-triazolo-(1,5-c)pyrimidine-2-sulfonamide (Compound 2) or a mixture comprising two parts of Thifensulfuron:one part Tribenuron-methyl (Compound 3), were prepared by admixing a predetermined amount of the compound with a predetermined quantity of water, a predetermined amount of 2,4-D and a predetermined amount of the surfactant X-77 to give aqueous dispersion containing varying amounts of one of Compound 1, 2 or 3, as the sole toxicant.

Corn, sorghum and wheat seeds were planted in beds of good agricultural peat based growth medium and grown in a greenhouse. After the plants had emerged and had grown to a height of about 4-5 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for eight days under greenhouse conditions conducive for good plant growth. At the end of this period, the beds were examined to determine the percentage of phytotoxicity to the corn, sorghum and wheat plants. The results of these examinations are set forth below in Table XII.

TABLE XII

| Test mixture | Treating Rate in g ae/ha* | pH | % Growth reduction as a % of control at indicated g ai/ha** | | | | | | | | |
|---|---|---|---|---|---|---|---|---|---|---|---|
| | | | corn | | | wheat | | | sorghum | | |
| | | | 17.5 | 8.8 | 4.4 | 17.5 | 8.8 | 4.4 | 17.5 | 8.8 | 4.4 |
| Compound 1/NA | 0.00 | 7.85 | 22.5 | 25.0 | 15.0 | 12.5 | 12.5 | 10.0 | 55.0 | 40.0 | 45.0 |
| Compound 1 + 2,4-D | 280.00 | 2.98 | 15.0 | 15.0 | 10.0 | 5.0 | 0.0 | 0.0 | 40.0 | 35.0 | 35.0 |
| Compound 1 + 2,4-D | 140.00 | 3.24 | 10.0 | 10.0 | 10.0 | 5.0 | 0.0 | 0.0 | 37.5 | 37.5 | 30.0 |
| Compound 1 + MCPA | 280.00 | 3.02 | 17.5 | 10.0 | 5.0 | 5.0 | 0.0 | 0.0 | 40.0 | 35.0 | 35.0 |
| Compound 1 + MCPA | 140.00 | 3.34 | 15.0 | 12.5 | 5.0 | 5.0 | 0.0 | 0.0 | 40.0 | 35.0 | 35.0 |
| Compound 2/NA | 0.00 | 7.80 | 37.5 | 22.5 | 15.0 | 10.0 | 5.0 | 2.5 | 60.0 | 55.0 | 50.0 |
| Compound 2 + 2,4-D | 280.00 | 2.99 | 20.0 | 15.0 | 5.0 | 7.5 | 0.0 | 0.0 | 25.0 | 25.0 | 25.0 |
| Compound 2 + 2,4-D | 140.00 | 3.27 | 10.0 | 7.5 | 2.5 | 7.5 | 0.0 | 0.0 | 27.5 | 27.5 | 25.0 |
| Compound 2 + MCPA | 280.00 | 3.04 | 30.0 | 20.0 | 12.5 | 5.0 | 5.0 | 0.0 | 40.0 | 40.0 | 35.0 |
| Compound 2 + MCPA | 140.00 | 3.33 | 30.0 | 20.0 | 5.0 | 0.0 | 0.0 | 0.0 | 40.0 | 40.0 | 35.0 |
| Compound 3/NA | 0.00 | 7.82 | 75.0 | 32.5 | 30.0 | 12.5 | 7.5 | — | 65.0 | 40.0 | 30.0 |
| Compound 3 + 2,4-D | 280.00 | 2.99 | 10.0 | 0.0 | 0.0 | 5.0 | 5.0 | — | 10.0 | 7.5 | 10.0 |
| Compound 3 + 2,4-D | 140.00 | 3.25 | 2.5 | 0.0 | 0.0 | 10.0 | 5.0 | — | 0.0 | 0.0 | 0.0 |
| Compound 3 + MCPA | 280.00 | 3.01 | 32.5 | 25.0 | 15.0 | 5.0 | 0.0 | — | 25.0 | 20.0 | 10.0 |
| Compound 3 + MCPA | 140.00 | 3.35 | 17.5 | 17.5 | 12.5 | 5.0 | 0.0 | — | 20.0 | 10.0 | 10.0 |
| control | — | 8.06 | 0.0 | | | 0.0 | | | 0.0 | | |

NA = no acid control
*grams of acid equivalent per hectare.
**grams of active ingredient per hectare.

EXAMPLE XIII

Representative compositions of the present invention were evaluated to determine their phytotoxicity effect in post-emergent operations on sorghum plants.

Aqueous dispersions containing one of N-(2,6-difluorophenyl)-5-methyl-1,2,4-triazolo-(1,5-a)pyrimidine-2-sulfonamide or Thifensulfuron, as the active ingredient, were prepared by admixing a predetermined amount of the compound with a predetermined quantity of water, a predetermined amount of one of 2,4-D and a predetermined amount of the surfactant X-77 to give aqueous dispersions containing varying amounts of the compound, as the sole toxicant.

Sorghum seeds were planted in beds of good agricultural peat based growth medium and grown in a greenhouse. After the plants had grown to a height of about 3 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for twelve days under greenhouse conditions conducive for good plant growth. At the end of this period, the beds were examined to determine the percentage of phytotoxicity to the sorghum plants. The results of these examinations are set forth below in Table XIII.

TABLE XIII

| Test mixture | Treating Rate in g ae/ha* | pH | % Growth reduction as a % of control at indicated g ai/ha** | |
|---|---|---|---|---|
| | | | 17.5 | 8.8 |
| N-(2,6-difluorophenyl)-5-methyl-1,2,4-triazolo-(1,5-a)pyrimidine-2-sulfonamide/NA | 0.0 | 7.50 | 55,0 | 55.0 |
| N-(2,6-difluorophenyl)-5-methyl-1,2,4-triazolo-(1,5-a)pyrimidine-2-sulfonamide + 2,4-D | 280.0 | 3.10 | 10.0 | 10.0 |
| Thifensulfuron/NA | 0.00 | 7.83 | 60.0 | 60.0 |
| Thifensulfuron + 2,4-D | 280.00 | 3.08 | 10.0 | 20.0 |

TABLE XIII-continued

| Test mixture | Treating Rate in g ae/ha* | pH | % Growth reduction as a % of control at indicated g ai/ha** | |
|---|---|---|---|---|
| | | | 17.5 | 8.8 |
| control | — | 7.85 | 0.0 | 0.0 |

NA = no acid control
*grams of acid equivalent per hectare.
**grams of active ingredient per hectare.

EXAMPLE XIV

Representative compositions of the present invention were evaluated to determine their phytotoxicity effect in post-emergent operations on sorghum plants.

Aqueous dispersions containing one of N-(2,6-difluorophenyl)-5-methyl-1,2,4-triazolo-(1,5-a)pyrimidine-2-sulfonamide or Thifensulfuron, as the active ingredient, were prepared by admixing a predetermined amount of the compound with a predetermined quantity of water, a predetermined amount of one of clopyralid and a predetermined amount of the surfactant X-77 to give aqueous dispersions containing varying amounts of the compound, as the sole toxicant.

Sorghum seeds were planted in beds of good agricultural peat based growth medium and grown in a greenhouse. After the plants had grown to a height of about 3 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for twelve days under greenhouse conditions conducive for good plant growth. At the end of this period, the beds were examined to determine the percentage of phytotoxicity to the sorghum plants. The results of these examinations are set forth below in Table XIV.

EXAMPLE XV

Representative compositions of the present invention were evaluated to determine their phytotoxicity effect in post-emergent operations on sorghum plants.

Aqueous dispersions containing N-(2,6-difluorophenyl)-5-methyl-1,2,4-triazolo-(1,5-a)pyrimidine-2-sulfonamide, as the active ingredient, were prepared by admixing a predetermined amount of the compound with a predetermined quantity of water, a predetermined amount of one of 2,4-D, MCPA and dicamba and a predetermined amount of the surfactant X-77 to give aqueous dispersions containing varying amounts of the compound, as the sole toxicant.

Sorghum seeds were planted in beds of good agricultural peat based growth medium and grown in a greenhouse. After the plants had grown to a height of about 3-4 inches, separate beds of the plants were sprayed with one of the above-prepared compositions at predetermined treating rates in grams of the active ingredient per hectare (g ai/ha). Other beds were treated only with a water-surfactant mixture, containing no active compound, and others containing the active compound and surfactant, but no acid, to serve as controls. After treatment, the beds were maintained for 13 days under greenhouse conditions conducive for good plant growth. At the end of this period, the beds were examined to determine the percentage of phytotoxicity to the sorghum plants. The results of these examinations are set forth below in Table XV.

TABLE XIV

| Test mixture | Treating Rate in g ae/ha* | pH | % Growth reduction as a % of control at indicated g ai/ha** | |
|---|---|---|---|---|
| | | | 17.5 | 8.8 |
| N-(2,6-difluorophenyl)-5-methyl-1,2,4-triazolo-(1,5-a)pyrimidine-2-sulfonamide/NA | 0.0 | 7.50 | 55.0 | 55.0 |
| N-(2,6-difluorophenyl)-5-methyl-1,2,4-triazolo(1,5-a)pyrimidine-2-sulfonamide + clopyralid | 140.0 | 2.67 | 30.0 | 30.0 |
| Thifensulfuron/NA | 0.00 | 7.83 | 60.0 | 60.0 |
| Thifensulfuron + clopyralid | 140.0 | 2.67 | 20.0 | 15.0 |
| control | — | 7.85 | 0.0 | 0.0 |

NA = no acid control
*grams of acid equivalent per hectare.
**grams of active ingredient per hectare.

TABLE XV

| Test mixture | Treating Rate in g ae/ha* | pH | % Growth reduction as a % of control at indicated g ai/ha** | | |
|---|---|---|---|---|---|
| | | | 35.0 | 11.7 | 3.5 |
| N-(2,6-difluorophenyl)-5-methyl-1,2,4-triazolo-(1,5-a)pyrimidine-2-sulfonamide/NA | 0.0 | 7.42 | 90.0 | 85.0 | 65.0 |
| N-(2,6-difluorophenyl)-5-methyl-1,2,4-triazolo-(1,5-a)pyrimidine-2-sulfonamide + 2,4-D | 280.0 | 2.93 | 35.0 | 30.0 | 25.0 |
| N-(2,6-difluorophenyl)-5-methyl-1,2,4-triazolo-(1,5- | 280.0 | 2.93 | 30.0 | 27.5 | 25.0 |

TABLE XV-continued

| Test mixture | Treating Rate in g ae/ha* | pH | % Growth reduction as a % of control at indicated g ai/ha** | | |
|---|---|---|---|---|---|
| | | | 35.0 | 11.7 | 3.5 |
| a)pyrimidine-2-sulfonamide + MCPA | | | | | |
| N-(2,6-difluorophenyl)-5-methyl-1,2,4-triazolo-(1,5-a)pyrimidine-2-sulfonamide + dicamba | 280.0 | 2.59 | 25.0 | 15.0 | 7.5 |
| control | — | 7.62 | 0.0 | 0.0 | 0.0 |

NA = no acid control
*grams of acid equivalent per hectare.
**grams of active ingredient per hectare.

EXAMPLE XVI

Representative compositions of the present invention were evaluated to determine their phytotoxicity effect in pre-emergent operations on corn and wheat plants.

Aqueous dispersions containing N-(2,6-difluorophenyl)-5-methyl-1,2,4-triazolo-(1,5-a)pyrimidine-2-sulfonamide, as the active ingredient, were prepared by admixing a predetermined amount of the compound with a predetermined quantity of water and a predetermined amount of 2,4-D to give aqueous dispersions containing varying amounts of the compound, as the sole toxicant.

Separate beds of good agricultural loamy sand containing 3.8 percent organic matter were sprayed with one of the above-prepared compositions at predetermined treating rates in grams of the active ingredient per hectare (g ai/ha) and the composition was then incorporated therein. Other beds were treated with no active compound to serve as a control. After treatment, the beds were seeded with corn and wheat seeds and maintained for 13 days under greenhouse conditions conducive for seed germination and good plant growth. At the end of this period, the beds were examined to determine the percentage of phytotoxicity as growth reduction of the seedlings as compared to the growth found in the control beds. The results of these examinations are set forth below in Table XVI.

What is claimed is:

1. A solid herbicidal formulation concentrate composition comprising, as the active material, a herbicidally effective amount of a sulfonamide or sulfonylurea herbicide from the group consisting of
   Chlorimuron-ethyl,
   Chlorsulfuron,
   Metsulfuron-methyl,
   Tribenuron-methyl,
   Thifensulfuron,
   N-(2,6-dichloro-3-methylphenyl)-5,7-dimethoxy-1,2,4-triazolo-(1,5-a)pyrimidine-2-sulfonamide,
   N-(2,6-dichlorophenyl)-5-ethoxy-7-fluoro-1,2,4-triazolo-(1,5-c)pyrimidine-2-sulfonamide,
   N-(2-chloro-6-fluorophenyl)-5-ethoxy-7-fluoro-1,2,4-triazolo-(1,5-c)pyrimidine-2-sulfonamide,
   N-(2,6-difluorophenyl)-8-chloro-5-methoxy-1,2,4-triazolo-(1,5-c)pyrimidine-2-sulfonamide,
   N-(2,6-difluorophenyl)-5-methyl-1,2,4-triazolo-(1,5-a)pyrimidine-2-sulfonamide,
   N-(2,6-difluorophenyl)-5-methoxy-8-fluoro-1,2,4-triazolo-(1,5-c)pyrimidine-2-sulfonamide, and
   2-(((7-fluoro-5-ethoxy-1,2,4-triazolo-(1,5-c)pyrimidine-2-yl)sulfonyl)amino)-3-fluorobenzoic acid, methyl ester,
or mixtures of said compounds, in admixture with an amount of a herbicidal organic acid from the group consisting of

TABLE XVI

| Test mixture | Treating Rate in g ae/ha* | pH | % Growth reduction as a % of control at indicated g ai/ha** | | | | | |
|---|---|---|---|---|---|---|---|---|
| | | | corn | | | wheat | | |
| | | | 140.0 | 70.0 | 35.0 | 140.0 | 70.0 | 35.0 |
| N-(2,6-difluorophenyl)-5-methyl-1,2,4-triazolo-(1,5-a)-pyrimidine-2-sulfonamide/NA | 0.0 | 6.10 | 46.7 | 30.0 | 23.3 | 53.3 | 30.0 | 23.3 |
| N-(2,6-difluorophenyl)-5-methyl-1,2,4-triazolo-(1,5-a)-pyrimidine-2-sulfonamide + 2,4-D | 560.0 | 3.07 | 20.0 | 6.7 | 8.3 | 46.7 | 25.0 | 25.0 |
| N-(2,6-difluorophenyl)-5-methyl-1,2,4-triazolo-(1,5-a)-pyrimidine-2-sulfonamide + 2,4-D | 280.0 | 3.05 | 6.7 | 6.7 | 3.3 | 30.0 | 11.7 | 10.0 |
| N-(2,6-difluorophenyl)-5-methyl-1,2,4-triazolo-(1,5-a)-pyrimidine-2-sulfonamide + 2,4-D | 140.0 | 3.09 | 23.3 | 10.0 | 8.3 | 28.3 | 8.3 | 6.7 |
| N-(2,6-difluorophenyl)-5-methyl-1,2,4-triazolo-(1,5-a)-pyrimidine-2-sulfonamide + 2,4-D | 70.0 | 3.50 | 28.3 | 13.3 | 8.3 | 36.7 | 6.7 | 8.3 |
| control | — | 7.74 | 0.0 | 0.0 | 0.0 | 0.0 | 0.0 | 0.0 |

NA = no acid control
*grams of acid equivalent per hectare.
**grams of active ingredient per hectare.

clopyralid,
2,4-D,
2,4-DP,
dicamba,
dichlorprop-P,
fluroxypyr
MCPA,
MCPP,
mecoprop-P,
picloram,
triclopyr or mixtures of said acids
sufficient to maintain the pH of the composition when it is in a water diluted formulation to below 5.

2. A composition as defined in claim 1 wherein the active compound is Chlorimuron-ethyl.

3. A composition as defined in claim 2 wherein the acid is 2,4-D.

4. A composition as defined in claim 2 wherein the acid is MCPA.

5. A composition as defined in claim 1 wherein the active compound is Chlorsulfuron.

6. A composition as defined in claim 5 wherein the acid is 2,4-D.

7. A composition as defined in claim 5 wherein the acid is MCPA.

8. A composition as defined in claim 1 wherein the active compound is Metsulfuron-methyl.

9. A composition as defined in claim 8 wherein the acid is 2,4-D.

10. A composition as defined in claim 8 wherein the acid is MCPA.

11. A composition as defined in claim 1 wherein the active compound is Tribenuron-methyl.

12. A composition as defined in claim 11 wherein the acid is 2,4-D.

13. A composition as defined in claim 11 wherein the acid is MCPA.

14. A composition as defined in claim 11 wherein the acid is dicamba.

15. A composition as defined in claim 1 wherein the active compound is Thifensulfuron.

16. A composition as defined in claim 15 wherein the acid is 2,4-D.

17. A composition as defined in claim 15 wherein the acid is MCPA.

18. A composition as defined in claim 15 wherein the acid is dicamba.

19. A composition as defined in claim 1 wherein the active compound is N-(2,6-dichloro-3-methylphenyl)-5,7-dimethoxy-1,2,4-triazolo-(1,5-a)pyrimidine-2-sulfonamide.

20. A composition as defined in claim 19 wherein the acid is 2,4-D.

21. A composition as defined in claim 19 wherein the acid is MCPA.

22. A composition as defined in claim 1 wherein the active compound is N-(2,6-dichlorophenyl)-5-ethoxy-7-fluoro-1,2,4-triazolo-(1,5-c)pyrimidine-2-sulfonamide.

23. A composition as defined in claim 22 wherein the acid is 2,4-D.

24. A composition as defined in claim 22 wherein the acid is MCPA.

25. A composition as defined in claim 22 wherein the acid is dicamba.

26. A composition as defined in claim 22 wherein the acid is picloram.

27. A composition as defined in claim 22 wherein the acid is clopyralid.

28. A composition as defined in claim 1 wherein the active compound is N-(2-chloro-6-fluorophenyl)-5-ethoxy-7-fluoro-1,2,4-triazolo-(1,5-c)pyrimidine-2-sulfonamide.

29. A composition as defined in claim 28 wherein the acid is 2,4-D.

30. A composition as defined in claim 28 wherein the acid is MCPA.

31. A composition as defined in claim 1 wherein the active compound is N-(2,6-difluorophenyl)-8-chloro-5-methoxy-1,2,4-triazolo-(1,5-c)pyrimidine-2-sulfonamide 32. A composition as defined in claim 31 wherein the acid is 2,4-D.

33. A composition as defined in claim 31 wherein the acid is MCPA.

34. A composition as defined in claim 31 wherein the acid is clopyralid.

35. A composition as defined in claim 1 wherein the active compound is N-(2,6-difluorophenyl)-5-methoxy-8-fluoro-1,2,4-triazolo-(1,5-c)pyrimidine-2-sulfonamide.

36. A composition as defined in claim 35 wherein the acid is 2,4-D.

37. A composition as defined in claim 35 wherein the acid is MCPA.

38. A composition as defined in claim 35 wherein the acid is clopyralid.

39. A composition as defined in claim 1 wherein the active compound is N-(2,6-difluorophenyl)-5-methyl-1,2,4-triazolo-(1,5-a)pyrimidine-2-sulfonamide.

40. A composition as defined in claim 39 wherein the acid is 2,4-D.

41. A composition as defined in claim 39 wherein the acid is MCPA.

42. A composition as defined in claim 39 wherein the acid is dicamba.

43. A composition as defined in claim 39 wherein the acid is clopyralid.

44. A composition as defined in claim 39 wherein the acid is picloram.

45. A composition as defined in claim 1 wherein the active compound is 2-(((7-fluoro-5-ethoxy-1,2,4-triazolo-(1,5-c)pyrimidin-2-yl)sulfonyl)amino)-3-fluorobenzoic acid, methyl ester.

46. A composition as defined in claim 45 wherein the acid is 2,4-D.

47. A composition as defined in claim 45 wherein the acid is MCPA.

48. A composition as defined in claim 45 wherein the acid is dicamba.

49. A composition as defined in claim 45 wherein the acid is clopyralid.

50. A composition as defined in claim 45 wherein the acid is picloram.

51. An aqueous herbicide formulation composition comprising, as the active material, a herbicidally effective amount of a sulfonamide or sulfonylurea herbicide from the group consisting of
Metsulfuron-methyl,
Chlorimuron-ethyl,
Tribenuron-methyl,
Chlorsulfuron,
Thifensulfuron,
N-(2,6-dichloro-3-methylphenyl)-5,7-dimethoxy-1,2,4-triazolo-(1,5-a)-pyrimidine-2-sulfonamide,
N-(2,6-dichlorophenyl)-5-ethoxy-7-fluoro-1,2,4-triazolo-(1,5-c)pyrimidine-2-sulfonamide,
N-(2-chloro-6-fluorophenyl)-5-ethoxy-7-fluoro-1,2,4-triazolo-(1,5-c)pyrimidine-2-sulfonamide, N-(2,6-difluorophenyl)-8-chloro 5-methoxy-1,2,4-triazolo-(1,5-c)pyrimidine-2-sulfonamide, N-(2,6-difluorophenyl)-5-methoxy-8-fluoro-1,2,4-triazolo-(1,5-c)pyrimidine-2-sulfonamide, N-(2,6-difluorophenyl)-5-methyl-1,2,4-triazolo-(1,5-a)pyrimidine-2-sulfonamide, and 2-(((7-fluoro-5-ethoxy-1,2,4-triazolo-(1,5-c)pyrimidin-2-yl)sulfonyl)amino)-3-fluorobenzoic acid, methyl ester in admixture with an amount of a herbicidal organic acid from the group consisting of clopyralid,
2,4-D,
2,4-DP,
dicamba,
dichlorprop-P,
fluroxypyr
MCPA,
MCPP,
mecoprop-P,
picloram,
triclopyr or mixtures of said acids sufficient to maintain the pH of the composition to below 5, a surfactant and water.

52. A composition as defined in claim 51 wherein the active compound is Chlorimuron-ethyl.

53. A composition as defined in claim 52 wherein the acid is 2,4-D.

54. A composition as defined in claim 52 wherein the acid is MCPA.

55. A composition as defined in claim 51 wherein the active compound is Chlorsulfuron.

56. A composition as defined in claim 55 wherein the acid is 2,4-D.

57. A composition as defined in claim 55 wherein the acid is MCPA.

58. A composition as defined in claim wherein the active compound is Metsulfuron-methyl.

59. A composition as defined in claim 58 wherein the acid is 2,4-D.

60. A composition as defined in claim 58 wherein the acid is MCPA.

61. A composition as defined in claim 51 wherein the active compound is Tribenuron-methyl.

62. A composition as defined in claim 61 wherein the acid is 2,4-D.

63. A composition as defined in claim 61 wherein the acid is MCPA.

64. A composition as defined in claim 61 wherein the acid is dicamba.

65. A composition as defined in claim 51 wherein the active compound is Thifensulfuron.

66. A composition as defined in claim 65 wherein the acid is 2,4-D.

67. A composition as defined in claim 65 wherein the acid is MCPA.

68. A composition as defined in claim 65 wherein the acid is dicamba.

69. A composition as defined in claim 51 wherein the active compound is N-(2,6-dichloro-3-methylphenyl)-5,7-dimethoxy-1,2,4-triazolo-(1,5-a)pyrimidine-2-sulfonamide.

70. A composition as defined in claim 70 wherein the acid is 2,4-D.

71. A composition as defined in claim 70 wherein the acid is MCPA.

72. A composition as defined in claim 51 wherein the active compound is N-(2,6-dichlorophenyl)-5-ethoxy-7-fluoro-1,2,4-triazolo-(1,5-c)pyrimidine-2-sulfonamide.

73. A composition as defined in claim 72 wherein the acid is 2,4-D.

74. A composition as defined in claim 72 wherein the acid is MCPA.

75. A composition as defined in claim 72 wherein the acid is dicamba.

76. A composition as defined in claim 72 wherein the acid is picloram.

77. A composition as defined in claim 72 wherein the acid is clopyralid.

78. A composition as defined in claim 51 wherein the active compound is N-(2-chloro-6-fluorophenyl)-5-ethoxy-7-fluoro-1,2,4-triazolo-(1,5-c)pyrimidine-2-sulfonamide.

79. A composition as defined in claim 78 wherein the acid is 2,4-D.

80. A composition as defined in claim 78 wherein the acid is MCPA.

81. A composition as defined in claim 51 wherein the active compound is N-(2,6-difluorophenyl)-8-chloro 5-methoxy-1,2,4-triazolo-(1,5-c)pyrimidine-2-sulfonamide.

82. A composition as defined in claim 81 wherein the acid is 2,4-D.

83. A composition as defined in claim 81 wherein the acid is MCPA.

84. A composition as defined in claim 81 wherein the acid is clopyralid.

85. A composition as defined in claim 51 wherein the active compound is N-(2,6-difluorophenyl)-5-methoxy-8-fluoro-1,2,4-triazolo-(1,5-c)pyrimidine-2-sulfonamide.

86. A composition as defined in claim 85 wherein the acid is 2,4-D.

87. A composition as defined in claim 85 wherein the acid is MCPA.

88. A composition as defined in claim 85 wherein the acid is clopyralid.

89. A composition as defined in claim 51 wherein the active compound is N-(2,6-difluorophenyl)-5-methyl-1,2,4-triazolo-(1,5-a)pyrimidine-2-sulfonamide.

90. A composition as defined in claim 89 wherein the acid is 2,4-D.

91. A composition as defined in claim 89 wherein the acid is MCPA.

92. A composition as defined in claim 89 wherein the acid is dicamba.

93. A composition as defined in claim 89 wherein the acid is clopyralid.

94. A composition as defined in claim 89 wherein the acid is picloram.

95. A composition as defined in claim 51 wherein the active compound is 2-(((7-fluoro-5-ethoxy-1,2,4-triazolo-(1,5-c)pyrimidin-2-yl)sulfonyl)amino)-3-fluorobenzoic acid, methyl ester.

96. A composition as defined in claim 95 wherein the acid is 2,4-D.

97. A composition as defined in claim 95 wherein the acid is MCPA.

98. A composition as defined in claim 95 wherein the acid is dicamba.

99. A composition as defined in claim 95 wherein the acid is clopyralid.

100. A composition as defined in claim 95 wherein the acid is picloram.

101. A method for reducing the phytotoxicity toward grassy crop plants of sulfonamide and sulfonylurea herbicides employed in the selective kill and control of broadleaf weeds growing in the presences of said grassy crop plants which comprises contacting said plants or their habitat with a herbicidally effective amount of an aqueous formulation containing a surfactant and water, and as the active material, a sulfonamide or sulfonylurea herbicide from the group consisting of Metsulfuron-methyl,
Chlorimuron-ethyl,
Tribenuron-methyl,
Chlorsulfuron,
Thifensulfuron,
N-(2,6-dichloro-3-methylphenyl)-5,7-dimethoxy-1,2,4-triazolo-(1,5-a)pyrimidine-2-sulfonamide,
N-(2,6-dichlorophenyl)-5-ethoxy-7-fluoro-1,2,4-triazolo-(1,5-c)pyrimidine-2-sulfonamide,
N-(2-chloro-6-fluorophenyl)-5-ethoxy-7-fluoro-1,2,4-triazolo-(1,5-c)pyrimidine-2-sulfonamide,
N-(2,6-difluorophenyl)-8-chloro 5-methoxy-1,2,4-triazolo-(1,5-c)pyrimidine-2-sulfonamide,
N-(2,6-difluorophenyl)-5-methoxy-8-fluoro-1,2,4-triazolo-(1,5-c)pyrimidine-2-sulfonamide,
N-(2,6-difluorophenyl)-5-methyl-1,2,4-triazolo-(1,5-a)pyrimidine-2-sulfonamide, and
2-(((7-fluoro-5-ethoxy-1,2,4-triazolo-(1,5-c)pyrimidine-2-yl)sulfonyl)amino)-3-fluorobenzoic acid, methyl ester, in admixture with an amount of a herbicidal organic acid from the group consisting of clopyralid,
2,4-D,
2,4-DP,
dicamba,
dichlorprop-P,
fluroxypyr
MCPA,
MCPP,
mecoprop-P,
picloram,
triclopyr or mixtures of said acids sufficient to maintain the pH of the formulation to below 5.

102. A method as defined in claim 101 wherein the active compound is Chlorimuron-ethyl.

103. A method as defined in claim 102 wherein the acid is 2,4-D.

104. A method as defined in claim 102 wherein the acid is MCPA.

105. A method as defined in claim 101 wherein the active compound is Chlorsulfuron.

106. A method as defined in claim 105 wherein the acid is 2,4-D.

107. A method as defined in claim 105 wherein the acid is MCPA.

108. A method as defined in claim 101 wherein the active compound is Metsulfuron-methyl.

109. A method as defined in claim 108 wherein the acid is 2,4-D.

110. A method as defined in claim 108 wherein the acid is MCPA.

111. A method as defined in claim 101 wherein the active compound is Tribenuron-methyl.

112. A method as defined in claim 111 wherein the acid is 2,4-D.

113. A method as defined in claim 111 wherein the acid is MCPA.

114. A method as defined in claim 111 wherein the acid is dicamba.

115. A method as defined in claim 101 wherein the active compound is Thifensulfuron.

116. A method as defined in claim 115 wherein the acid is 2,4-D.

117. A method as defined in claim 116 wherein the acid is MCPA.

118. A method as defined in claim 115 wherein the acid is dicamba.

119. A method as defined in claim 101 wherein the active compound is N-(2,6-dichloro-3-methylphenyl)-5,7-dimethoxy-1,2,4-triazolo-(1,5-a)pyrimidine-2-sulfonamide.

120. A method as defined in claim 119 wherein the acid is 2,4-D.

121. A method as defined in claim 119 wherein the acid is MCPA.

122. A method as defined in claim 101 wherein the active compound is N-(2,6-dichlorophenyl)-5-ethoxy-7-fluoro-1,2,4-triazolo-(1,5-c)pyrimidine-2-sulfonamide.

123. A method as defined in claim 122 wherein acid is 2,4-D.

124. A method as defined in claim 122 wherein the acid is MCPA.

125. A method as defined in claim 122 wherein the acid is dicamba.

126. A method as defined in claim 122 wherein the acid is picloram.

127. A method as defined in claim 122 wherein the acid is clopyralid.

128. A method as defined in claim 101 wherein the active compound is N-(2-chloro-6-fluorophenyl)-5-ethoxy-7-fluoro-1,2,4-triazolo-(1,5-c)pyrimidine-2-sulfonamide.

129. A method as defined in claim 128 wherein the acid is 2,4-D.

130. A method as defined in claim 128 wherein the acid is MCPA.

131. A method as defined in claim 101 wherein the active compound is N-(2,6-difluorophenyl)-8-chloro-5-methoxy-1,2,4-triazolo-(1,5-c)pyrimidine-2-sulfonamide.

132. A method as defined in claim 131 wherein the acid is 2,4-D.

133. A method as defined in claim 131 wherein the acid is MCPA.

134. A method as defined in claim 131 wherein the acid is clopyralid.

135. A method as defined in claim 101 wherein the active compound is N-(2,6-difluorophenyl)-5-methoxy-8-fluoro-1,2,4-triazolo-(1,5-c)pyrimidine-2-sulfonamide.

136. A method as defined in claim 135 wherein the acid is 2,4-D.

137. A method as defined in claim 135 wherein the acid is MCPA.

138. A method as defined in claim 135 wherein the acid is clopyralid.

139. A method as defined in claim 101 wherein the active compound is N-(2,6-difluorophenyl)-5-methyl-1,2,4-triazolo-(1,5-a)pyrimidine-2-sulfonamide.

140. A method as defined in claim 139 wherein the acid is 2,4-D.

141. A method as defined in claim 139 wherein the acid is MCPA.

142. A method as defined in claim 139 wherein the acid is dicamba.

143. A method as defined in claim 139 wherein the acid is clopyralid.

144. A method as defined in claim 139 wherein the acid is picloram.

145. A method as defined in claim 101 wherein the active compound is 2-(((7-fluoro-5-ethoxy-1,2,4-triazolo-(1,5-c)pyrimidin-2-yl)sulfonyl)amino)-3-fluorobenzoic acid, methyl ester.

146. A method as defined in claim 145 wherein the acid is 2,4-D.

147. A method as defined in claim 145 wherein the acid is MCPA.

148. A method as defined in claim 145 wherein the acid is dicamba.

149. A method as defined in claim 145 wherein the acid is clopyralid.

150. A method as defined in claim 145 wherein the acid is picloram.

* * * * *

REEXAMINATION CERTIFICATE (2847th)
United States Patent [19]
Noveroske

[11] B1 5,236,887
[45] Certificate Issued Apr. 16, 1996

[54] HERBICIDAL HETEROCYCLIC SULFONYLUREA COMPOSITIONS SAFENED BY HERBICIDAL ACIDS SUCH AS 2,4-D BELOW A PH OF 5

[75] Inventor: Robert L. Noveroske, Midland, Mich.

[73] Assignee: Dow Elanco, Indianapolis, Ind.

Reexamination Request:
No. 90/003,929, Aug. 29, 1995

Reexamination Certificate for:
Patent No.: 5,236,887
Issued: Aug. 17, 1993
Appl. No.: 695,194
Filed: May 3, 1991

[51] Int. Cl.$^6$ .......................... A01N 25/32; A01N 47/36; A01N 43/40; A01N 37/10
[52] U.S. Cl. .......................... 504/105; 504/110; 504/130; 504/135; 504/136; 504/139
[58] Field of Search .................................. 504/105, 110, 504/130, 135, 136, 139

[56] References Cited
U.S. PATENT DOCUMENTS
5,017,215  5/1991  Ackerson et al. .......................... 71/93

FOREIGN PATENT DOCUMENTS
0318433  11/1988  European Pat. Off. .

OTHER PUBLICATIONS

"Herbicidal sulfonamide combinations" (17941), *Research Disclosure*, Mar. 1979, pp. 122–123.

"Herbicidal sulfonamide combinations" (18149), *Research Disclosure*, May 1979, p. 246.

*Primary Examiner*—S. Mark Clardy

[57] ABSTRACT

Disclosed are herbicidal concentrate formulation compositions having reduced grass crop plant phytotoxicity comprising certain sulfonamide or sulfonylurea herbicides in admixture with a herbicidal organic acid from the group consisting of clopyralid, 2,4-D, 2,4-DP, dicamba, dichlorprop-P, fluroxypyr MCPA, MCPP, mecoprop-P, picloram, triclopyr or mixtures of said acids; also disclosed is the preparation of said compositions and the pre- and post-emergent agricultural uses thereof in water diluted form.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5–7 and 55–57 are cancelled.

Claims 1, 51 and 101 are determined to be patentable as amended.

Claims 2–4, 8–50, 52–54, 58–100 and 102–150, dependent on an amended claim, are determined to be patentable.

1. A solid herbicidal formulation concentrate composition comprising, as the active material, a herbicidally effective amount of a sulfonamide or sulfonylurea herbicide from the group consisting of
   Chlorimuron-ethyl,
   [Chlorsulfuron,]
   Metsulfuron-methyl,
   Tribenuron-methyl,
   Thifensulfuron,
   N-(2,6-dichloro-3-methylphenyl)-5,7-dimethoxy-1,2,4-triazolo-(1,5-a)pyrimidine-2-sulfonamide,
   N-(2,6-dichlorophenyl)-5-ethoxy-7-fluoro-1,2,4-triazolo-(1,5-c)pyrimidine-2-sulfonamide,
   N-(2-chloro-6-fluorophenyl)-5-ethoxy-7-fluoro-1,2,4-triazolo-(1,5-c)pyrimidine-2-sulfonamide,
   N-(2,6-difluorophenyl)-8-chloro-5-methoxy-1,2,4-triazolo-(1,5-c)pyrimidine-2-sulfonamide,
   N-(2,6-difluorophenyl)-5-methyl-1,2,4-triazolo-(1,5-a)pyrimidine-2-sulfonamide,
   N-(2,6-difluorophenyl)-5-methoxy-8-fluoro-1,2,4-triazolo-(1,5-c)pyrimidine-2-sulfonamide, and
   2-(((7-fluoro-5-ethoxy-1,2,4-triazolo-(1,5-c)pyrimidine-2-yl)sulfonyl)amino)-3-fluorobenzoic acid, methyl ester,
or mixtures of said compounds, in admixture with an amount of a herbicidal organic acid from the group consisting of
   clopyralid,
   2,4-D,
   2,4-DP,
   dicamba,
   dichlorprop-P,
   fluroxypyr,
   MCPA,
   MCPP,
   mecoprop-P,
   picloram,
   triclopyr or mixtures of said acids
sufficient to maintain the pH of the composition when it is in a water diluted formulation [to] below 5.

51. An aqueous herbicide formulation composition comprising, as the active material, a herbicidally effective amount of a sulfonamide or sulfonylurea herbicide from the group consisting of
   Metsulfuron-methyl,
   Chlorimuron-ethyl,
   Tribenuron-methyl,
   [Chlorsulfuron,]
   Thifensulfuron,
   N-(2,6-dichloro-3-methylphenyl)-5,7-dimethoxy-1,2,4-triazolo-(1,5-a)-pyrimidine-2-sulfonamide,
   N-(2,6-dichlorophenyl)-5-ethoxy-7-fluoro-1,2,4-triazolo-(1,5-c)pyrimidine-2-sulfonamide,
   N-(2-chloro-6-fluorophenyl)-5-ethoxy-7-fluoro-1,2,4-triazolo-(1,5-c)pyrimidine-2-sulfonamide,
   [N-(2,6-difluorophenyl)-8-chloro 5-methoxy-1,2,4-triazolo-(1,5-c)pyrimidine-2-sulfonamide,]
   *N-(2,6-difluorophenyl)-8-chloro-5-methoxy-1,2,4-triazolo-(1,5-a)pyrimidine-2-sulfonamide,*
   N-(2,6-difluorophenyl)-5-methoxy-8-fluoro-1,2,4-triazolo-(1,5-c)pyrimidine-2-sulfonamide,
   N-(2,6-difluorophenyl)-5-methyl-1,2,4-triazolo-(1,5-a)pyrimidine-2-sulfonamide, and
   2-(((7fluoro-5-ethoxy-1,2,4-triazolo-(1,5-c)pyrimidin-2-yl)sulfonyl)amino)-3-fluorobenzoic acid, methyl ester
in admixture with an amount of a herbicidal organic acid from the group consisting of
   clopyralid,
   2,4-D,
   2,4-DP,
   dicamba,
   dichlorprop-P,
   fluroxypyr,
   MCPA,
   MCPP,
   mecoprop-P,
   picloram,
   triclopyr or mixtures of said acids
sufficient to maintain the pH of the composition [to] below 5, a surfactant and water.

101. A method for reducing the phytotoxicity toward grassy crop plants of sulfonamide and sulfonylurea herbicides employed in the selective kill and control of broadleaf weeds growing in the [presences] *presence* of said grassy crop plants which comprises contacting said plants or their habitat with a herbicidally effective amount of an aqueous formulation containing a surfactant and water, and as the active material, a sulfonamide or sulfonylurea herbicide from the group consisting of
   Metsulfuron-methyl,
   Chlorimuron-ethyl,
   Tribenuron-methyl,
   Chlorsulfuron,
   Thifensulfuron,
   N-(2,6-dichloro-3-methylphenyl)-5,7-dimethoxy-1,2,4-triazolo-(1,5-a)pyrimidine-2-sulfonamide,
   N-(2,6-dichlorophenyl)-5-ethoxy-7-fluoro-1,2,4-triazolo-(1,5-c)pyrimidine-2-sulfonamide,
   N-(2-chloro-6-fluorophenyl)-5-ethoxy-7-fluoro-1,2,4-triazolo-(1,5-c)pyrimidine-2-sulfonamide,
   [N-(2,6-difluorophenyl)-8-chloro 5-methoxy-1,2,4-triazolo-(1,5-a)pyrimidine-2-sulfonamide,]

N-(2,6-difluorophenyl)-8-chloro-5-methoxy-*1,2,4*-*triazolo-(1,5-a)pyrimidine-2-sulfonamide,*

N-(2,6-difluorophenyl)-5-methoxy-8-fluoro-1,2,4-triazolo-(1,5-a)pyrimidine-2-sulfonamide, N-(2,6-difluorophenyl)-5-methyl-1,2,4-triazolo-(1,5-a)pyrimidine-2-sulfonamide, and 2-(((7-fluoro-5-ethoxy-1,2,4-triazolo-(1,5-c)pyrimidine-2-yl)sulfonyl)amino)-3-fluorobenzoic acid, methyl ester, in admixture with an amount of a herbicidal organic acid from the group consisting of clopyralid, 2,4-D, 2,4-DP, dicamba, dichlorprop-P, fluroxypyr

MCPA,

MCPP, mecoprop-P, picloram, triclopyr or mixtures of said acids sufficient to maintain the pH of the formulation [to] below 5, *the quantity of said formulation applied being such that the application rate of said acid or acids is between about 15 and about 1200 grams per hectare.*

* * * * *